United States Patent
Gjørsvik et al.

(10) Patent No.: US 11,565,123 B2
(45) Date of Patent: Jan. 31, 2023

(54) DEVICE FOR PHOTODYNAMIC TREATMENT

(71) Applicant: PHOTOCURE ASA, Oslo (NO)

(72) Inventors: Tore Gjørsvik, Gjerdrum (NO); Aslak Godal, Oslo (NO); Roger William Rolfe Warren, Pukekohe (NZ)

(73) Assignee: PHOTOCURE ASA, Oslo (NO)

( * ) Notice: Subject to any disclaimer, the term of this patent is extended or adjusted under 35 U.S.C. 154(b) by 58 days.

(21) Appl. No.: 16/875,391

(22) Filed: May 15, 2020

(65) Prior Publication Data

US 2020/0276450 A1    Sep. 3, 2020

Related U.S. Application Data

(63) Continuation of application No. 16/063,203, filed as application No. PCT/EP2016/081425 on Dec. 16, 2016, now abandoned.

(30) Foreign Application Priority Data

Dec. 18, 2015 (GB) .................. 1522398

(51) Int. Cl.
*A61N 5/06* (2006.01)
*A61B 5/20* (2006.01)

(52) U.S. Cl.
CPC ........... *A61N 5/062* (2013.01); *A61B 5/202* (2013.01); *A61N 5/0603* (2013.01); *A61N 2005/061* (2013.01); *A61N 2005/0642* (2013.01)

(58) Field of Classification Search
CPC .......... A61N 5/062; A61N 5/0603; A61N 2005/0642; A61N 2005/061; A61N 2005/0651; A61B 5/202; A61M 25/1018; A61M 25/04; A61M 25/10; A61K 41/0061; A61K 31/19
See application file for complete search history.

(56) References Cited

U.S. PATENT DOCUMENTS

| | | |
|---|---|---|
| 5,496,271 A | 3/1996 | Burton |
| 6,645,230 B2 | 11/2003 | Whitehurst |
| 2010/0016844 A1 | 1/2010 | Patel, Jr. |
| 2014/0235942 A1 | 8/2014 | Hellstrom et al. |

FOREIGN PATENT DOCUMENTS

| | | |
|---|---|---|
| WO | 1996/028412 A1 | 9/1996 |
| WO | 1999/053962 A1 | 10/1999 |
| WO | 2002/010120 A1 | 2/2002 |
| WO | 2003/041673 A2 | 5/2003 |
| WO | 2005-092838 A1 | 10/2005 |
| WO | 2009/074811 A2 | 6/2009 |

(Continued)

OTHER PUBLICATIONS

Beyer, W., "Systems for Light Application and Dosimetry in Photodynamic Therapy"; J. of PhotoChem and PhotoBio (1996); vol. 36; pp. 153-156.

(Continued)

*Primary Examiner* — Mark W. Bockelman
(74) *Attorney, Agent, or Firm* — Fox Rothschild LLP

(57) ABSTRACT

A catheter device for use in the photodynamic treatment of a body cavity or hollow organ of the body, such as the bladder, the device being used in the photodynamic treatment of abnormalities, disorders or diseases of the internal surfaces of said body cavity or hollow organ.

23 Claims, 4 Drawing Sheets

(56) References Cited

FOREIGN PATENT DOCUMENTS

| WO | 2009/077960 A1 | 6/2009 |
|---|---|---|
| WO | 2010/072419 A2 | 7/2010 |
| WO | 2010/142456 A1 | 12/2010 |
| WO | 2010/142457 A1 | 12/2010 |
| WO | 2011/161220 A1 | 12/2011 |
| WO | 2012/004399 A1 | 1/2012 |
| WO | 2014/020164 A1 | 2/2014 |
| WO | 2015/006309 A1 | 1/2015 |

OTHER PUBLICATIONS

Eichenauer, R. H. et al., "A New Ballon Catheter System Used for PDT in the Human Urinary Bladder, Accuracy of Light Distribution" SPIE (1998); vol. 3247; pp. 138-144.
Fotinos, N. et al., "5-Aminolevulinic Acid Derivatives in Photomedicine Characteristics, Application and Perspectives"; J. PhotoChem and PhotoBio (2006); vol. 82: pp. 994-1015.
Johnansson, A. et al., "Photodynamic Management for Bladder Cancer"; Proc. of SPIE (2009); vol. 7380; pp. 73801S1-S9.
Kubin, A. et al., "Fluorescence Diagnosis of Bladder Cancer with New Water Soluble Hypercin Bound to Polyvinylpyrrolidone: PVP-Hypericin"; J. PhotoChem and PhotoBio (2008); vol. 84: pp. 1560-1563.
Skyrme, R. J. et al., "A Phase-1 Study of Sequential Mitomycing C and 5-Aminolaevulic Acid-mediated Photodynamic Therapy in Recurrecnt Superfical Bladder Carcinoma"; BJU International (2005); vol. 95; pp. 1206-1210.
Waidelich, R. et al., "Whole Bladder Photodynamic Therapy with 5-Aminolevulinic Acid Using a White Light Source"; Urology (2003); vol. 61:2; pp. 333-337.
Yavari, N. et al., "An Overview on Preclinical and Clinical Experiences with Photodynamic Therapy for Bladder Cancer"; Canadian Journal of Urology (2011); vol. 18:4; pp. 5778-5786.

Fig. 4
Fig. 5
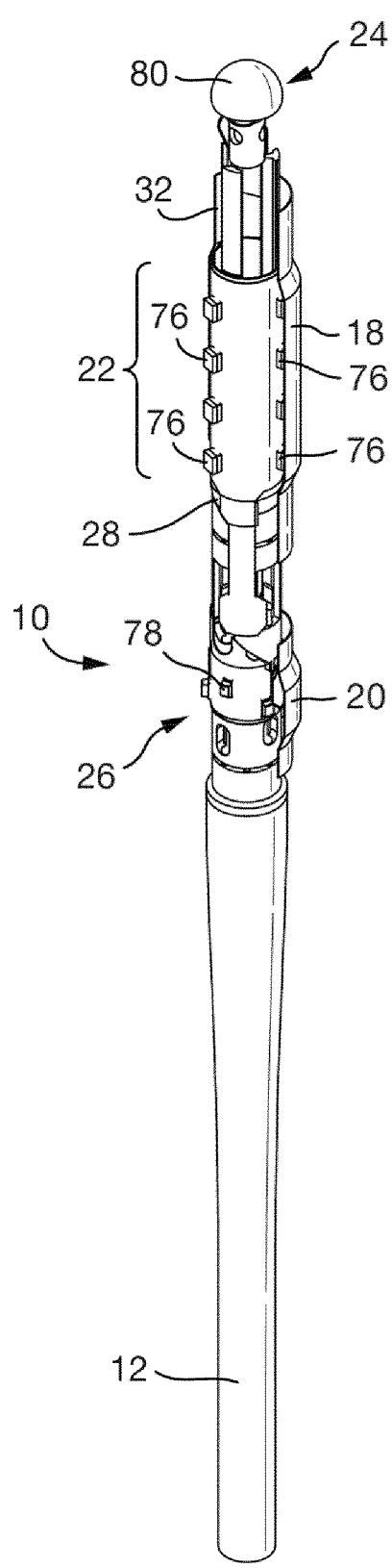
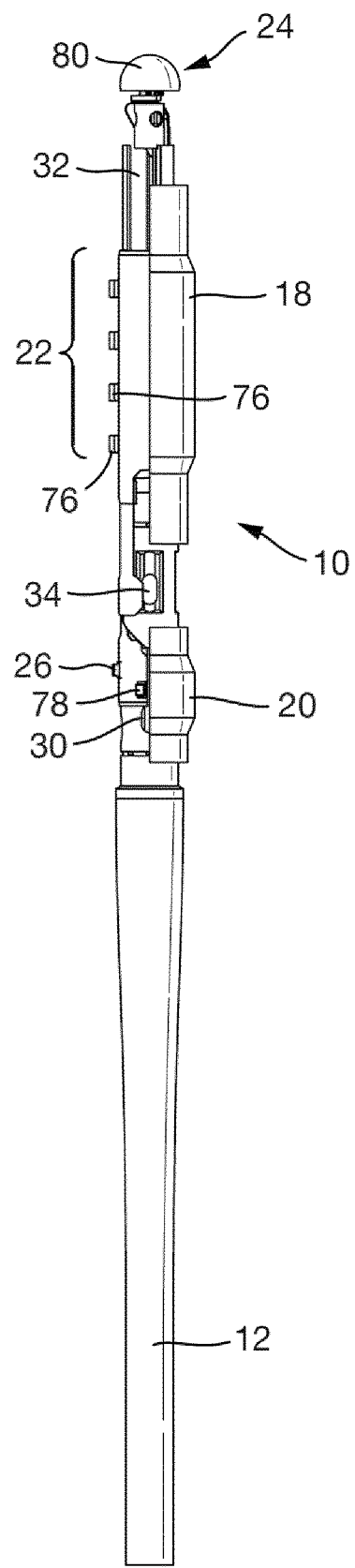

DEVICE FOR PHOTODYNAMIC TREATMENT

This invention relates to a device for use in the photodynamic treatment of a body cavity or hollow organ of the body, such as the bladder, and to the use of such a device in the photodynamic treatment of abnormalities, disorders or diseases of the internal surfaces of said body cavity or hollow organ.

Photodynamic treatment (PDT) is a relatively new technique for the treatment of pre-cancerous conditions, cancer and non-cancerous diseases, such as infections and inflammation. PDT involves the administration of a photosensitiser or a precursor thereof to an area of interest. The photosensitiser or precursor thereof is taken up into the cells, where a precursor of a photosensitiser is converted into a photosensitiser. Upon exposure of the area of interest to light, the photosensitiser is excited, usually from a ground singlet state to an excited singlet state. It then undergoes intersystem crossing to a longer-lived excited triplet state. One of the few chemical species present in tissue with a ground triplet state is molecular oxygen. When the photosensitiser and an oxygen molecule are in proximity, an energy transfer can take place that allows the photosensitiser to relax to its ground singlet state, and create an excited singlet state oxygen molecule. Singlet oxygen is a very aggressive chemical species and will very rapidly react with any nearby biomolecules.

Ultimately, these destructive reactions will kill cells through apoptosis or necrosis, whereby for instance cancer cells are selectively killed. The mechanisms are still not fully understood, but studies suggest that the clinical result, e.g. the selectivity for cancerous cells, is not due to selective uptake by cancerous cells. Rather, there are similar levels of uptake in all cell types, but the processes of conversion and elimination are different in malignant cells and generally in metabolically active cells, such as inflamed or infected cells, leading to a concentration gradient between cancerous and normal tissue.

Various photosensitisers and precursors of photosensitisers are known and described in the art.

Typical photosensitisers include dyes like hypericin and PVP hypericin, psoralens, porphyrins such as hematoporphyrins, protoporphyrins, uroporphyrins, coproporphyrins, benzoporphyrins or deuteroporphyrins, in particular Photofrin® (porfimer sodium), photosan III or verteporfin; chlorins, including bacteriochlorins and isochlorins such as chlorine e6, talaporfin or temoporfin and phthalocyanines such as aluminium- and silicon phthalocyanines.

Typical precursors of photosensitisers include 5-aminolevulinic acid (5-ALA) and certain derivatives thereof, e.g. 5-ALA N-derivatives or 5-ALA esters. Such compounds are intracellularly converted protoporphyrins, such as protoporphyrin IX (PpIX), which are photosensitisers. Currently several pharmaceutical products comprising 5-ALA or 5-ALA esters are in clinical use for PDT. One of them is Metvix®, a topical dermal product in the form of a cream comprising 5-ALA methyl ester (Galderma, Switzerland) for the photodynamic treatment of actinic keratosis and basal cell carcinoma. Another known product is Levulan Kerastick® (DUSA Pharmaceuticals, Canada), a solution for the photodynamic treatment of actinic keratosis which contains 5-ALA.

It is known to use 5-ALA esters clinically for the detection of cancer in the bladder. In the known technique, Hexvix® (Photocure ASA, Norway), a solution comprising 5-ALA hexyl ester is instilled into the bladder and the bladder surface is exposed to blue light. In response, PpIX displays a red fluorescence which is detected. Cancerous cells display a higher fluorescence than normal cells and hence cancerous lesions can be detected. This technique is known as photodynamic diagnosis (PDD).

5-ALA, 5-ALA hexyl ester and several other photosensitisers such as Photofrin® have been used experimentally in pre-clinical and clinical studies for the photodynamic treatment of bladder cancer (for review: N. Yavari et al., Can J Urol. 2011, 18(4), 5778-86). The management of superficial cancerous lesions in the bladder is challenging: when considered slightly aggressive, the disease may recur for many years and lead to a progressive loss of bladder function; whereas when aggressive, it may progress to an invasive tumour and lead to death in up to one third of the cases. Standard therapies are based on resection of cancerous lesions via transurethral bladder resection (TUR) and/or fulguration of all visible tumours, in association with different modalities of topical chemo- or immunotherapy, i.e. agents that are instilled into the bladder such as mitomycin C or bacillus Calmette-Guérin (BCG). However, such therapies fail in certain patients and there is thus a need for alternative treatment such as PDT.

The inner surface of the bladder, i.e. the bladder wall, is not smooth, but consists of a series of ridges known as rugae, which are produced by folding of the bladder wall. The function of the rugae is to allow the bladder to expand when needed. When the bladder is not full, the rugae are folds in the tissue. However, as the bladder fills with urine, it expands by unfolding the rugae. When the bladder empties again, it refolds and the rugae increase to their former size. For bladder PDT, these rugae present a challenge since the whole bladder wall needs to be exposed to light such that no cancerous lesions are missed.

In some prior art techniques, this problem was addressed as follows: either the bladder was filled with sufficient volume of saline solution to produce a smooth bladder wall (R. Skyrme et al., BJU Int. 2005, 95(5), 1206-1210) or a continuous irrigation with saline solution was maintained during the whole PDT procedure at a flushing pressure sufficient to distend the bladder without folds (A. Johansson et al., Proc. of SPIE Vol. 7380, 73801S1-S9, 2009).

Both procedures are quite cumbersome, since the bladder size/volume varies from patient to patient and the filling volume or flushing pressure for continuous irrigation has to be determined for each patient before the PDT procedure and the bladder volume has to be controlled during the course of the PDT procedure, usually by suprapubic ultrasound (see for instance R. Waidelich et al., Urology 2003, 61(2), 332-337). Also, the complexity of the equipment increases with the presence of one or more lumen to introduce or circulate the saline solution in the bladder and thus patients may need general anaesthesia during PDT (see R. Waidelich, supra) or spinal anaesthesia (R. Skyrme et al., BJU Int. 2005, 95(5), 1206-1210).

In some cases new medical devices have been proposed. In R. Waidelich, supra, a catheter is equipped with a Foley balloon for securing the catheter in the bladder and an optical fibre supplies light to a scattering rod intended to distribute light across the internal surface during irrigation with saline to keep the surface smooth. Another proposal (W. Beyer, Journal of Photochemistry and Photobiology B: Biology 36 (1996) 153-156) uses a light applicator for bladder PDT using two concentric transparent balloons. An outer balloon, inflated by water, fills the bladder and touches the outer wall, stretching it to a smooth surface. An inner balloon is filled with a fat emulsion as a scattering medium and distributes light from an optic fibre with a conical end.

In the prior art devices discussed above a light source outside the body is used with light transmitted to a point within the body via an optic fibre, where it is then diffused or scattered via the end of the optic fibre and/or through an additional diffuser type device. With these types of systems it is difficult to achieve a simple arrangement for a uniform distribution of light. In addition, the requirement for a relatively high-powered and high-intensity light source outside of the body means that specialist equipment and additional training is required to enable medical staff to carry out the required PDT.

The light passing through the prior art optic fibres will always be travelling generally along the longitudinal axis of the catheter in the forward direction, i.e. in a distal direction along the direction of the longitudinal axis. As a result, projecting light in all directions to provide coverage throughout the entirety of the inner surface of the body cavity or hollow organ requires a relatively complex redistribution of the direction of the light and illumination of the inner surface at the entrance to the body cavity or hollow organ is difficult to achieve. In contrast, with the device proposed above, by placing a light source within the body and by the use of a plurality of light emitting elements located in different regions then it becomes possible to direct light in all of the required directions, including at the entrance to the hollow organ or body cavity, with a very even distribution and with a relatively simple design. Surprisingly, it has been found that light emitting elements placed within the body in this way can easily provide the required wavelengths and intensity of light whilst remaining very compact and therefore able to be used by a catheter device even when a relatively small catheter is used, for example for treatment of the bladder and approaching via the urethra. The device can also be sufficiently small and flexible to allow for use with just a local anaesthesia, rather than a general anaesthesia (which is required for larger and more rigid devices).

In the prior art discussed above, the light source required to generate the required wavelengths at the necessary intensity through transmission along the optic fibre would generally need to be a laser or a high-powered xenon short arc lamp, for example. As noted above this is a relatively complex item of equipment and often would not be readily available to medical staff, as well as requiring extra training, safety precautions and/or safety equipment.

According to a first aspect the present invention provides a catheter device for use in the photodynamic treatment of a body cavity or hollow organ of the body, the catheter device comprising: a distal end portion having a longitudinal axis and being for insertion into the body cavity or hollow organ, the distal end portion including: an expansion and positioning balloon for expanding within the body cavity or hollow organ and thereby distending an outer wall of the body cavity or hollow organ, and a light source located on the distal end portion so as to be within the body cavity or hollow organ when the catheter device is in use; wherein the light source comprises a plurality of light emitting elements arranged to: project light forward in a distal direction along the direction of the longitudinal axis from a first region of the distal end, project light outwardly of the longitudinal axis from a second region of the distal end, the second region being at least partly within the expansion and positioning balloon, and project light around the point of entry of the catheter device into the body cavity or hollow organ from a third region of the distal end, the third region being closer to the point of entry of the catheter device into the body cavity or hollow organ than the second region; and the distal end portion also including a second balloon for retaining the distal end within the body cavity or hollow organ, the second balloon being spaced apart from the expansion and positioning balloon and centred on a location closer to a proximal end of the catheter device than a centre of the expansion and positioning balloon.

With the arrangement proposed above since the light source is contained within the device then no specialist equipment outside of the device is required. Instead, only a power source is necessary, and this may easily be provided along with the catheter device. Advantageously, it has been found that light emitters within the body can provide the required intensity and time of treatment even when powered by batteries, which further increases the benefits of the proposed systems compared to the prior art optic fibre based devices. Surprisingly, it has been found that the use of light emitting elements within a hollow organ or body cavity does not result in excessively high temperatures and can easily provide a system that will not heat body tissues above safe temperatures for treatment of the body, for example a system that remains below 43° C. In some examples these safe temperatures can be maintained simply based on the available heat absorption within the body cavity or hollow organ of interest and the heat dissipation to the rest of the body that is possible. Alternatively, or in addition, heat may optionally be removed by means of the catheter device, for example through exchange of liquids with the outside of the body, and/or cooling may be provided before treatment, for example by use of fluids at below body temperature to expand the positioning and expansion balloon.

In WO 2015/006309 a device is discussed primarily in context of light transmitted via an optical fibre system, but mention is also made of the possible use of light emitters within the body such as LEDs, although without any discussion of refinements as set forth herein. The device or WO 2015/006309 may include a single balloon for inflation to position light delivery elements at a minimum distance from a target tissue. However, the device of the first aspect set out above differs in significant respects from the device of WO 2015/006309 through the use of a specific arrangement of light emitting elements in different regions, with particular purposes, and via the combination of this with the use of two balloons, where an expansion and positioning balloon at least partly contains the second region of the light emitting elements, and a separate second balloon is provided for retaining the device within the body cavity or hollow organ.

With the proposed device the expansion and positioning balloon advantageously allows for correct positioning of the device within the body cavity or hollow organ and a suitable distance between body tissue and the light emitting elements, whilst the separate second balloon can retain the distal end within the body cavity or hollow organ with or without inflation of the expansion and positioning balloon. Thus, the proposed device can be operated in various modes including only the second balloon inflated, or with both balloons inflated, such as for flushing of the body cavity or hollow organ before or after treatment, instillation of photosensitiser, photodynamic treatment and so on, as discussed in more detail below. The expansion and positioning balloon may be arranged to centre the device in relation to the expanded shape of the hollow organ or body cavity such that there can be a required minimum light dose for all parts of the interior of the hollow organ or body cavity, and optionally an even light dose across all parts thereof. The expansion and positioning balloon may also act as a safety device, ensuring sufficient distance between the light emitting elements and the body tissue and preventing over-heating and/or an overdose of light.

The proposed device is therefore considered to be able to provide improved PDT through better distribution of light, as well as increased ease-of-use and reduced inconvenience to the patient. In fact, it is possible that the device can be used by medical personnel with conventional training in the use of catheters and in an outpatient setting, for example at a urology clinic for treatment of the bladder. As noted above, only local rather than general anaesthesia is required.

The term "distal" refers to a direction away from the physician (or other medical personnel using the device), which is also the direction of insertion of the device into the body. The "proximal" direction is hence the direction toward the physician, and the direction toward the opposite end of the device to the distal end. The distal end might typically have a generally cylindrical body with the light source and the expansion and positioning balloon located within or on the cylindrical body along with other parts of the device. The longitudinal axis of the distal end of the proposed device would typically be aligned with the longitudinal axis of the catheter and thus would generally extend tangentially from the tubular body structure through which the catheter device is inserted into the body cavity or hollow organ, for example the urethra when the bladder is being treated. It should, however, be noted that the catheter device may be a steerable catheter device and/or may have a curved end for improved access to the body cavity organ of interest. In this case the longitudinal axis of the distal end may differ from the longitudinal axis of the catheter. For example, a Coude catheter type arrangement may be used for ease of access to the male bladder past the prostate.

In accordance with the first aspect the plurality of light emitting elements of the light source are arranged to project light forward in a distal direction along the direction of the longitudinal axis from the first region of the distal end; project light outwardly of the longitudinal axis from the second region of the distal end; and project light around the point of entry of the catheter device into the body cavity or hollow organ from the third region of the distal end. In example implementations, the plurality of light emitting elements may include one or more light emitting element(s) located at the first region, the second region and/or the third region. The light emitted from the first, second, and/or third region may be produced by light emitting elements located elsewhere on the distal end with light guiding devices such as lenses and/or reflectors being arranged to direct the light to the required region(s) and project the light in the required direction(s). In a preferred example, as explained further below, the plurality of light emitting elements includes at least one light emitting element at each of the first region, the second region and the third region, with the light emitting element(s) located at each region providing the light from that region.

The term "body cavity/hollow organ" refers to such cavities/organs that have non-smooth surfaces or rugae. This includes the vagina, the stomach, the intestines, the bladder and the gallbladder, and preferably refers to the bladder. The term "body cavity/hollow organ" should preferably be understood to exclude blood vessels, and hence in preferred embodiments the device is not for treatment of blood vessels.

It is envisaged that this device will be of particular use in treatment of the bladder. The proposed device will eliminate the need for liquid (e.g. saline) to distend the bladder wall in PDT as well as improving the distribution of light and the ease of the treatment of the bladder. Hence, in a preferred embodiment the device is for treatment of the bladder. Saline may still be instilled to the bladder (or other body organ) for cooling purposes or for "lubrication" in that the saline can ease the friction between the balloon and the bladder wall, but saline is not needed for distension of the bladder.

The use of a light source provided as a part of the catheter device and used within the body, and the consequent avoidance of the need for specialist training and/or equipment outside of the body means that the catheter device can be designed as a single use device with all parts in patient contact being disposable. Thus, in preferred implementation the catheter device is a disposable single use device. This may apply not only to the distal end portion of the device with the features described above, but also to parts of the proximal end of the catheter device, such as the power source, control circuitry, and/or fluid couplings and fluid propulsion devices as described in further detail below.

The light source will generally be electrically powered, with power being transmitted via electrical wires along the catheter from a power source outside of the body. Preferably the light source is powered by a battery or low voltage power source outside of the body.

The plurality of light emitting elements may be any suitable light emitting elements able to produce light at the required intensity and wavelength for the PDT of interest. Absorption spectra from photosensitisers known in the art are available in the literature, e.g. the absorption spectrum of PpIX, the photosensitiser which is the result of cellular conversion of precursors like 5-ALA or derivatives of 5-ALA, like 5-ALA esters, is disclosed in for instance U.S. Pat. No. 6,645,230, FIG. 9. N. Yavari et al., Can J Urol 18(4), 2011, 5778-5786 provide in Table 1 an overview over the main activation wavelength of various photosensitisers and precursors of photosensitisers. For precursors like 5-ALA or derivatives of 5-ALA, like 5-ALA esters, irradiation with wavelengths of light in the range of 300-800 nm, e.g. 400-700 nm and 500-700 nm has been found particularly effective and the light emitting elements may hence be selected for light at these wavelengths.

Red light (600-670 nm) is known to penetrate well into tissue and the use of red light in the PDT procedure may thus be useful to destroy abnormalities, e.g. neoplastic tissue, in deeper tissue layers. For the destruction of superficial lesions, blue light (400-500 nm) which is typically used in photodynamic diagnosis or green light (500-560 nm) may be used.

Alternatively, different wavelengths may be used to efficiently destroy superficial and deeper lesions. For instance white light irradiation has been used in bladder PDT with precursors like 5-ALA or derivatives of 5-ALA, like 5-ALA esters (see for instance A. Johansson et al., Proc. of SPIE Vol. 7380, 73801S1-S9, 2009 or R. Waidelich et al., Urology 2003, 61(2), 332-337).

In the case of treatment of the bladder, and similar PDT regimes, then red light is expected to be of most use and thus the light emitting elements may be arranged to produce light with a wavelength in the range 600-670 nm, for example a wavelength of about 635 nm.

The light source may project light to the walls of the hollow organ or body cavity of interest with fluence rates of no more than 100 mW/cm$^2$, and optionally 50 mW/cm$^2$ or less, such as a fluence rate in the range 10-35 mW/cm$^2$, for example a fluence rate of perhaps about 15-25 mW/cm$^2$. The timing of the treatment may be set in order to provide a light dose of 10 J/cm² to 100 J/cm². These types of fluence rates and light doses would provide effective PDT for the bladder and similar organs.

In preferred embodiments light emitting diodes (LEDs) are used as the light emitting elements of the light source. LEDs can provide a cheap and effective light source for the types of wavelengths and intensities that are required for a safe and efficient PDT, as well as being available in sufficiently small sizes. In one example LEDs with a footprint of 0.3 mm² or less are used. Using small LEDs of this type, preferably in combination with a flexible printed circuit board (PCB) at least for the central part of the array, allows for the device to be sufficiently flexible to be manoeuvred into the required position inside the body. For example, in the case of a device for treating the male bladder then the distal end must manoeuvre around the prostate. Alternatively, other light emitting elements can be used such as light emitting capacitors, field induced polymer electroluminescent lights or other similar technologies. What is important for the operation of the catheter device is the wavelength and the intensity of the light, the ability to have a plurality of small light emitting elements in the light source, and the avoidance of excessive heat. The device can use any light emitting elements providing the requisite capabilities, but at the present time LEDs are preferred, if only for cost reasons.

The light emitting elements preferably each emit light across a volume having the shape of a spherical sector, for example a spherical sector with an angle of 140° at its apex is typical. There may be lenses or a coating with scattering particles to focus or diffuse the light. The light emitting elements of the light source may each be placed adjacent to additional light emitting elements in each of the three regions so that the light from each light emitting element overlaps with the light from the adjacent light emitting elements.

The light emitting elements may be arranged in an array having multiple parts including some or all of a first, distal part located at the first region for projecting light forward in the distal direction, a second, central part located at the second region for projecting light outwardly from the longitudinal axis of the distal end of the catheter device, and a third, proximal part located at the third region for projecting light around the point of entry of the catheter device into the body cavity or hollow organ. Preferably the third region is outside the expansion and positioning balloon and the second region is at least partly inside, or fully inside the expansion and positioning balloon. The first region may be outside of the expansion and positioning balloon and is preferably at the opposite side of the balloon to the third region.

One or more of the three parts of the array of light emitting elements may preferably also project light in other directions. In particular, the light projected from the various parts of the array may overlap or at least will form a complete volume of projecting light for extending across the entire inner surface of the wall of the body cavity or hollow organ. Thus, the plurality of light emitting elements may be arranged to project light from within the body cavity or hollow organ onto a roughly spherical surface, with no shadows or non-illuminated regions, aside from of course at the opening to the body cavity or hollow organ (e.g. across the cross-section of the urethra where the bladder is treated) where the main body of the catheter will be present and naturally illumination is both not possible and also not required.

The first, distal part of the array may be arranged to project light forward in the distal direction and also in a volume encompassing at least a cone or spherical sector centred on the longitudinal axis of the distal end and broadening in diameter in the distal direction. The first part of the array may project light across a larger part of a sphere centred on the longitudinal axis of the distal end, including projecting some light outward normal to the longitudinal axis and optionally backward toward the proximal direction i.e. across a volume with the shape of a sphere with a spherical sector missing. Thus, the shadow in the light projected by the first part may be a cone (or spherical sector) centred on the longitudinal axis of the distal end and broadening in diameter in the proximal direction.

The second, central part of the array may be arranged to project light outwardly from the longitudinal axis of the distal end, i.e. in directions extending normal to the axis. The second part may be arranged to project light both normal to the axis and also in volumes extending forward and backward along the distal and proximal directions, thereby illuminating a volume of the form of a cylinder or sphere centred on the longitudinal axis of the distal end with conical shadows/non-illuminated regions at either end of the cylinder and centred on the longitudinal axis.

The third, proximal part of the array may be arranged to project light in a similar manner to the second part, but from the third region which is closer to the entrance to the hollow organ or body cavity than the second region. The third part may project light in a volume encompassing a cylinder or sphere with two conical shadows/non-illuminated regions at either end of the cylinder and centred on the longitudinal axis. Since it is always necessary with a catheter device for a part of the catheter to pass through the tubular body structure that forms the entrance to the body cavity or hollow organ then, as mentioned above, there will always be a shadow at the opening to the body cavity or hollow organ where illumination is not possible. By the use of a second part with a location at a second region and an additional third part with a location at a third region that is closer to the point of entry than the second region then the effect of the "shadow" from the body of the catheter is minimised and a full and effective illumination of the inside of the hollow organ or body cavity can be achieved.

It will be understood that in some circumstances the extent of the second region and the extent of the third region could be such that the two regions will meet. Thus, the array of light emitting elements could include a combined second and third part extending across the second and third regions. However, it is considered that an even distribution of light at the required intensity can be achieved if there is separation between the second region and the third region, which then may provide advantages in the structure of the device, for example in relation to space for fluid outlets and/or connection points for the expansion and positioning balloon, as discussed in more detail below.

The first part of the array may be at the tip of the distal end of the catheter device, and preferably includes at least one light emitting element at the tip facing in the distal direction, as well as optionally additional light emitting elements located around the tip and facing outward from the direction of the longitudinal axis of the distal end, i.e. normal thereto, and/or facing in directions at an angle between the normal to the longitudinal axis and the distal direction. There may be a cluster of light emitting elements at the tip facing in the distal direction. It is preferred that all of the light emitting elements in the first part are arranged such that the light from each light emitting element overlaps with the light from one or more adjacent light emitting elements in the first part.

The second part of the array may be fully within the expansion and positioning balloon and preferably the second region extends across a centre of the expansion and positioning balloon and/or across a location that is at a centre of the body cavity or hollow organ when the device is in use. The second part of the array may include a plurality of light emitting elements spaced around and along the longitudinal axis of the distal end, for example around a cylindrical shape centred on the longitudinal axis. In example implementations there are multiple rings of light emitting elements with at least three light emitting elements in each ring and at least three rings placed adjacent one another along the longitudinal axis of the distal end. For example, there may be four rings each made of four light emitting elements. It is preferred that all of the light emitting elements in the second part are arranged such that the light from each light emitting element overlaps with the light from one or more adjacent light emitting elements in the second part.

In a preferred arrangement the second part of the array comprises a flexible printed circuit board holding the light emitting elements, the flexible printed circuit board being wrapped in a cylindrical fashion in order to form a generally cylindrical shape holding the light emitting elements of the central part. The light emitting elements on the flexible printed circuit board may be arranged to form a spiral about the cylindrical shape of the central part.

The third part of the array may have a similar form to the second part, but would typically have a lesser extent in the direction along the longitudinal axis of the distal end. The third part of the array may hence include a plurality of light emitting elements spaced around and along the longitudinal axis of the distal end, for example around a cylindrical shape centred on the longitudinal axis. In example implementations there is at least one ring of light emitting elements with at least three light emitting elements in the ring and at least one or more rings placed adjacent one another along the longitudinal axis of the distal end. For example, there may be two rings each made of four light emitting elements. It is preferred that all of the light emitting elements in the third part are arranged such that the light from each light emitting element overlaps with the light from one or more adjacent light emitting elements in the third part.

In example embodiments where the catheter device is for treatment of the bladder then the proximal part is advantageously able to provide effective illumination of the bladder trigone, which is not possible with prior art devices. Thus, a catheter device for treatment of the bladder may have a light source including a third part located at a third region of the distal end, wherein in use the third region sits adjacent and or within the bladder trigone in order to illuminate the trigone walls.

Power for each part of the array of light emitting elements may be supplied from the same power source, and preferably a single pair of wires is used to provide power for all of the light emitting elements. The light source may include a circuit for coupling all of the light emitting elements to the power source. The light emitting elements may be simply coupled in series, but preferably both parallel and serial connections are used in the circuit, with parallel connections to keep the voltage low and serial connections to avoid the possibility of one faulty LED consuming all the current. If all of the light emitting elements were identical then this would result in the same light intensity from each of the light emitting elements. However, it may be advantageous to allow for a different intensity of light from different light emitting elements, and in particular for the light emitting elements in the different regions. Thus, in some examples different types of light emitting elements or light emitting elements of the same type but providing light at different intensities are used in the different regions in order to obtain a required distribution of light intensity. In some examples the circuit for coupling the light emitting elements to the power source may have three power channels (for example LED driver circuits) for the three regions/three parts of the array. This allows for individual tuning of each channel to achieve a required light distribution. The circuit for coupling the light emitting elements to the power source may include an external light emitting element coupled to the light emitting elements of the distal end such that whenever the light emitting elements of the distal end are illuminated then the external light emitting element is also illuminated. This external light emitting element, which might be an LED for example, can provide a simple indication of an on-going photodynamic treatment.

The expansion and positioning balloon provides for a minimum distance between the light emitting elements and the bladder wall. This hence limits the maximum light dose and ensures a reliable high degree of uniformity of the minimum light dose. The expansion and positioning balloon and optionally the second balloon may act as a passive filter for some or all areas of the balloon and hence limit the light passing through in those areas in order to assist the uniformity of the light projected to the bladder wall. At least one of the expansion and positioning balloon or the second balloon may have a balloon skin comprising a light attenuating medium, such that the attenuation of light passing through the balloon skin varies depending on the level of inflation of the balloon in order to permit regulation of a light dose based on the level of inflation of the balloon. In this way the level of inflation of the balloon can regulate the light dose for the body tissue outside of the balloon. This can provide for automatic control of the light dose in a way that relates to the minimum distance of the body tissue from the light emitting elements, which may be determined by the distance between the light emitting elements and the outer surface of the balloon. The light dose received by an object varies with an inverse square relationship to the distance from the light source to the object. With a small body cavity or hollow organ, for example in the case of a smaller than average bladder, there may be a risk that the distance between the light emitting elements and the body tissue will be to small and an excessive light dose would be received if all of the light was transmitted through the balloon skin. By using a balloon skin having a light attenuating medium the amount of light that can pass through the balloon at a smaller inflation can be restricted compared to the amount of light at a larger inflation, and this risk is avoided. With suitable calibration for the light source and the light attenuating medium, it is possible to set the device up to treat a range of bladder sizes whilst delivering a known, constant irradiance level at the bladder wall that is independent of bladder size.

The light attenuating medium may be within the material of the balloon or on the surface of the balloon. The light attenuating medium may comprise a pigment or dye, which could be mixed into the material of the balloon skin during manufacture, or coated onto a surface of the balloon skin. Alternatively or additionally the light attenuating medium may comprise particles such as microparticles, nanoparticles or fibres such as microfibers. Thus, the light attenuating medium may generate a light attenuating effect by reflection or refraction of light by such particles. In one example particles are arrayed within the balloon skin so that when the balloon is relaxed then the gaps between particles are small, or the particles overlap, but when the balloon is expanded then the gaps between particles increase in size. Another possibility is for the light attenuating medium to include plasmonic particles such as gold nanoparticles. Such particles have a strong interaction with light at certain wavelengths in which electrons on the surface undergo a collective oscillation known as surface plasmon resonance (SPR). This can be used in controlling the absorption and scattering of light.

The expansion and positioning balloon may be a sheath along and around a part of the distal end when it is in its unexpanded form. In some example implementations this sheath encloses the second region and thus it may fully or partially enclose the second part of the array of light emitting elements. The sheath may sit as a single layer, or it may be at least partially in multiple layers with one or more eversion fold(s) where the sheath turns back on itself. A folded sheath can allow for a larger balloon with less elastic deformation of the balloon during expansion. In some cases the balloon may expand both elastically and plastically during use and in this instance the balloon may be larger when deflated after use than prior to deflation. Thus, the unexpanded form of the balloon may differ before and after expansion. In one example the balloon may be a single layer sheath prior to expansion, but may at least partially form multiple layers around the distal end when deflated after use. The distal end may have a narrower cross-section at the tip than within the expansion and positioning balloon in order that the double thickness of balloon skin can be held about the tip without the overall cross-section being increased. It will be appreciated that during withdrawal of the distal end from the body cavity or hollow organ then any loose material of the balloon will be slid toward the tip, and allowing a narrower cross-section at the tip means that the folded section of balloon can be accommodated whilst keeping the total cross-section of the distal end within a maximum diameter.

The expanded shape of the expansion and positioning balloon is preferably arranged for expansion of the relevant body cavity or hollow organ to produce a smooth wall for the internal surface thereof. The expansion and positioning balloon may for example have a generally spheroidal shape when expanded, including an oblate or prolate spheroid. The expanded shape of the expansion and positioning balloon may have hollows at its outer end where the balloon joins to the distal end of the catheter device. Thus, the expansion and positioning balloon may be arranged to bulge outwardly in the distal and/or the proximal direction along the longitudinal axis of the distal end such that the expansion and positioning balloon has a larger extent along the direction of the longitudinal axis when it is expanded than when it is unexpanded. With this in mind the expansion and positioning balloon may take the form of a spheroid with indentations in one or both ends, for example a shape similar to an apple, which may be a toroidal shape including a horn torus or spindle torus, as well as similar toroids based on ellipses or other shapes rather than on circles.

Advantageously, the first region, which may include a first part of the array of light emitting elements, may be located outside of the balloon at the distal end of the expansion and positioning balloon. In this case the expansion and positioning balloon preferably has a distal hollow at the distal end when it is expanded, wherein the first region is within the distal hollow. This means that the first region can emit light directly toward the wall of the body orifice or hollow organ beyond the distal end of the catheter device and that the light emitting elements at the first region can be on a tip of the distal end as well as in close proximity to the wall, whilst at the same time the expansion and positioning balloon will act to prevent contact of the tip and/or the light emitting elements with the wall. Thus, the expansion and positioning balloon, when expanded, preferably extends along the direction of the longitudinal axis of the distal end at least as far as the first region and/or the tip of the distal end. It can be important to avoid contact of the light emitting elements and/or the tip of the distal end with the wall of the body cavity or hollow organ since these parts may be relatively hard and hence could damage the tissue of the wall and also because the light emitting elements may also emit heat, which gives rise to another risk of damage to the tissue of the wall.

The size and volume of the expansion and positioning balloon will depend on the body cavity or hollow organ that is of interest. In the case of treatment of the bladder, the expansion and positioning balloon may be arranged to expand to a spheroidal or toroidal shape with an expanded diameter and/or height of between 40 mm and 100 mm, for example about 60 mm. This allows for the bladder wall to be expanded without the balloon necessarily filling the entirety of the bladder, so that there is still room for build-up of urine in the bladder and movement of fluid into and around the bladder, for example as a consequence of bodily functions, for cleaning or flushing the bladder and/or for conveying pharmaceutical compositions into the bladder such as a photosensitiser or precursor of a photosensitiser.

The second balloon may advantageously be a Foley balloon for expansion at the point of entry of the catheter device into the body cavity or hollow organ in order to prevent flow of fluid through the tubular body structure through which the catheter device is inserted and in order to secure the distal end of the catheter device in place within the body cavity or hollow organ. The third region of the distal end may be partially or fully within the Foley balloon, thereby ensuring that when in use the third region will be located at a known position relative to the point of entry of the catheter device into the body cavity or hollow organ. This means that light projected from light emitting elements at the third part of the array in the third region will reliably illuminate the wall of the body cavity or hollow organ around the point of entry. In the case of treatment of the bladder the use of a Foley balloon is well known and the Foley balloon of a catheter device for bladder treatment may be similar in form to conventional Foley balloons. For example, when the catheter device is for use with the bladder the Foley balloon may have a diameter of between 15 mm and 25 mm, for example diameter of approximately 20 mm.

The shape or location of the Foley balloon and the expansion and positioning balloon may be such that when both balloons are expanded there is a space or a channel for flow of fluid between the two balloons toward the longitudinal axis of the distal end. In one example this may be achieved by ensuring that the distance between the balloons cannot be bridged by the balloons even when fully expanded. Alternatively, one or both balloons may be provided with a contoured shape or an external element attached to the balloon even when the two balloons are fully expanded and in contact with another then a space or channel remains for flow of fluid between the balloons toward the longitudinal axis of the distal end.

The material of the balloon(s) may be any elastic material suitable for medical use and having an appropriate degree of transparency to the wavelengths required for treatment emitted from the light emitting elements. Preferably the balloon material is fully elastic and thus after being expanded it will return to its original unexpanded size and shape. Latex, silicone, PVC or rubbers can be used for the material for the balloon. Advantageously, the balloon and the catheter may be made of the same material. Having the catheter and the balloon made from the same material is beneficial as it is then easier to bond them together.

The balloon(s) may be formed on a mandrel by dipping and then later bonded to the body of the distal end. The balloon(s) may take the form of a sheath about the body of the distal end when in their unexpanded form. This may be a simple cylindrically tubular sheath, or it may be a more complex shape in order to reflect the intended shape of the balloon after it has been expanded. In one example the expansion and positioning balloon has an unexpanded shape taking the form of a tube with a varying diameter having a central cylindrical section at a first diameter flanked by two sections with decreasing diameter and the two ends at a second diameter, which is smaller than the first diameter. The diameter may decrease linearly in the two sections with decreasing diameter.

The distal end of the catheter device is preferably provided with at least one fluid inlet/outlet within the positioning and expansion balloon, and similarly within the Foley balloon when present. The balloon(s) may be expanded by injecting a fluid into the balloon via the catheter device. The fluid may be saline, for example. When there are light emitting elements within the balloon then the fluid may optionally include a light diffusing ingredient, for example a dissolved ingredient or a suspension of particles. However, it is envisaged that generally diffusion of light by the fluid will not be necessary to achieve the required even distribution of light, and therefore typically the fluid would be transparent to the wavelengths of light of interest. In example embodiments the catheter device has a single fluid passage both for supplying fluid and for removing fluid from the (or each) balloon. This minimises the space required on the body of the distal end as well as minimising the number of lumens needed in the catheter for fluid transport to the balloon(s). Alternatively, there may be one inlet opening and one outlet opening along with a corresponding pair of lumens for one or both balloons. This can allow for circulation of fluid through the balloon(s) in order to remove heat generated by the light emitting elements during the illumination required for PDT.

The body of the distal end is preferably provided with a fluid inlet and a fluid outlet for communication with the inside of the hollow organ or body cavity. This allows for circulation of fluid within the hollow organ or body cavity, outside of the balloon(s), for example for flushing out the bladder, as well as allowing for fluid to be drained from the hollow organ or body cavity or for fluid to be instilled into the hollow organ or body cavity.

For instance, when in use in the bladder, there may be a need to drain urine and/or blood from the bladder. Since blood absorbs light, the presence of blood may impact the PDT procedure and thus there may be a need to rinse the bladder (or other organ) from blood by instilling a fluid, e.g. saline, into the bladder and draining the bladder thereafter. Further, it may be beneficial to provide the organ with a liquid, e.g. a buffer or saline before the positioning and expansion balloon is expanded. The liquid will act as a spacer during distension of the organ during expansion of the balloon and can provide a lubricant effect. As noted above, it is not necessary with the proposed device to use saline or similar fluid for distension of the organ.

The catheter device generally includes an elongate catheter body extending from the distal end to a proximal end of the catheter device. This elongate catheter body may include lumens for transport of fluid to and from the various outlets, and optionally for passage of electrical wires, for example to provide power to the light source. Alternatively, the catheter body may include lumens for passage of fluid and wires embedded in walls of the catheter body. The latter arrangement can allow for a smaller diameter of the catheter body, which reduces patient discomfort in cases where the structure that connects the body cavity or hollow organ to the outside of the body is narrow in diameter, e.g. the urethra in case of the bladder. As well as wires for providing power to the light source the catheter body may also carry further wires, for example wires coupled to sensors at the distal end as discussed below. The catheter body may also carry an optical fibre to transmit light from inside to outside of the patient as an indicator that there is illumination at the distal end of the catheter device.

The outer diameter of the catheter body may be generally dependent on its use would generally be comparable to similar catheters of the art: for catheters to be used in fairly large organs like the stomach (i.e. inserted into the esophagus and ultimately into the stomach), the catheter may have a larger outer diameter than if inserted through the urethra into the bladder. The outer diameter is preferably small enough to fit within the portion of the body to which it is inserted to (esophagus, urethra) and to house internally contained components and lumens.

In preferred embodiments the catheter body comprises a flexible plastic or polymeric material suitable for medical use in general and catheter bodies in particular. Appropriate materials may include silicones, latex, rubbers, polyurethanes and combinations of these materials. Depending on its use, the catheter body may have an antiseptic coat to prevent bacterial infection of the body cavity/hollow organ or other body tissue it comes in contact with, e.g. the urethra, or an analgesic coat, e.g. a coat with lidocaine or similar local anesthetics.

The proximal end of the catheter body may be coupled to one or more external elements of the catheter device, for example a power source, one or more fluid reservoir(s) for inflation of the balloons(s) and/or for instilling fluid into the body orifice or hollow organ, a receptacle for receiving fluids flushed from the body orifice or hollow organ, and/or a controller. The external elements of the catheter device remain outside of the patient's body during use of the device.

The device may include one or more fluid reservoir(s) for inflation of the balloons(s), these fluid reservoir(s) advantageously taking the form of syringes or other manually actuatable devices such as an infusion bag for delivery of fluid into the balloon(s). If an infusion bag is used then the fluid flow from the bag into the body can be stopped using a clip/clamp and enabled by removing the clip/clamp. The fluid will run into the bladder by gravitational force. These are typical arrangements for a conventional Foley balloon. As a result, the device can be operated by anyone with the necessary training to use a conventional catheter equipped with a Foley balloon, and in any clinical setting with equipment suitable for purpose.

The fluid reservoir for instilling fluid into the body orifice or hollow organ could take the form of a bag supplying the catheter device through a drip type arrangement, or alternatively a syringe could be used. This can provide fluids for flushing the body orifice or hollow organ and/or it might also be used for instillation of the photosensitiser or precursor of a photosensitiser.

The catheter device may include a pressure activated device provided at the proximal end of the catheter body in order to provide an indication and/or a release of pressure in the event that the pressure within the expansion and positioning balloon and/or within the second balloon exceeds a threshold level. For example, there may be a safety balloon having larger stiffness than the expansion and positioning balloon and/or within the second balloon and connected to the same source of fluid, such that if the expansion and positioning balloon and/or within the second balloon experiences a pressure over a certain threshold then the safety balloon will inflate and provide a visual indication of an overpressure situation. Alternatively or additionally a pressure relief valve may be present, allowing for fluid to be vented from the system when there is an overpressure. A passive system such as a safety balloon or a passive pressure relief valve can provide a reliable way to ensure that a warning or a pressure release can be triggered when the pressure is too high. This type of a passive system allows for the pressure within the body to be monitored in a very simple way without the need for additional sensors or electronics within the distal end of the device, and this can aid in making a 'disposable' device that is suitable for single-use. In further alternatives, or in addition, the catheter device may include a pressure sensor, such as a pressure sensor linked with the controller mentioned below, although as noted above this can have the disadvantage of adding extra components within the distal end, and increasing the complexity of the electronics.

In one example implementation one of the external elements is a controller including a power source for the device. The controller may include control circuit, such as a microcontroller or microprocessor, for controlling the light source and for providing indications relating to operation of the device. In a preferred embodiment the control circuit comprises a timer arranged to provide activation of the light source after a preset time period and/or for a preset time period.

In addition the control circuit may be arranged to provide pulsed illumination. This can be achieved by providing a function generator within a microprocessor. Pulsed light may be advantageous in ensuring that no unacceptable heating of tissue occurs. In addition, providing intervals in illumination enhances tissue oxygenation and the effect of PDT. If a precursor of a photosensitiser such as 5-ALA or derivatives thereof are used for the PDT, which are converted to protoporphyrins, it allows for the re-accumulation of protoporphyrins and oxygen in surviving cells that can be treated with repeated illuminations. The frequency and length of the pulses can be chosen according to the requirements of the treatment regime and set within the control circuit. The control circuit may be programmable enabling it to be programmed by the user. This enables the length of illumination and the illumination pattern to be adjusted to suit individual treatments. In a preferred embodiment, the control circuit is not programmable by the user and only comprises features to start the device and indicators for the performance of the device as mentioned below.

Preferably the control circuit further comprises a display system for providing indications about the operation of the device. For example, the display may indicate the time elapse and/or time remaining for the PDT. One simple form for the display is a set of indicator lights such as LEDs.

Another optional feature of the control circuit is one or more performance indicator, such as a light or a sound emitter, for informing a user whether the device has operated correctly or whether a fault has occurred. In relation to this feature the distal end of the catheter device may preferably include one or more sensor for measuring a parameter relating to the performance of the device, for example the light dose, a temperature and/or a pressure.

A temperature at the distal end of the device may be measured in order to obtain an indication of the temperature of the walls of the body cavity or hollow organ. For example, the temperature of the fluid inside or outside of the balloon(s), the temperature of the body of the distal end, or the temperature of a PCB holding the light emitting elements may be measured, with a calculation then being made to relate this to a temperature of the wall of the body cavity or hollow organ, and an alert being provided if the measured temperature indicates a potentially excessive temperature at the wall of the body cavity or hollow organ, for example a temperature over 43° C. However, a temperature between body temperature of the patient and 43° C. is beneficial since it speeds up the photodynamic therapy. Consequently, it is not required nor beneficial to limit heat generation from the light source to body temperature and below.

A pressure sensor may be used to measure the pressure within one or both balloons in order to provide an indication of potential leakage or rupture, which would result in an unexpected change in the pressure. An additional pressure sensor may measure pressure within the bladder fluid outside of the balloon(s) with a differential between the pressure inside a balloon and the pressure outside of the balloon being used to determine if there has been a breach of the balloon. An alert may be provided by the control circuit in the event that the pressure sensor(s) provide readings indicative of a breach of a balloon.

Advantageously, the catheter device is designed for a single-use and for disposal after that single use. Preferably, the device includes one or more features that promote single-use and/or prevent repeat use. For example, the power source may be arranged to provide power that is only sufficient for a single-use, i.e. such that the power source is depleted after the required treatment is complete. The power source may be arranged so as not to be re-charged, and/or the control circuit may lack access to re-charge the power source. The control circuit may be arranged to prevent re-use by means of features of its programming, for example by permitting only a single activation of the light source, and/or it may include a deactivation mechanism that destroys circuitry or software when triggered.

The invention also extends to the catheter device of the first aspect or preferred embodiments thereof as discussed above when in a kit form comprising the catheter device and a photosensitiser or precursor thereof for PDT treatment. Suitable photosensitisers and precursors of photosensitisers are discussed below.

A resistance meter connected across the balloon wall may provide an additional or alternative way to identify a breach of a balloon. When the balloon wall ruptures then the resistance over the balloon wall will drop. This feature is considered novel and inventive in its own right and therefore, in an additional aspect, the present invention provides a catheter device for use in the treatment of a body cavity or hollow organ of the body, the catheter device comprising: a distal end portion having a longitudinal axis and being for insertion into the body cavity or hollow organ, the distal end portion including: an expansion and positioning balloon for expanding within the body cavity or hollow organ and thereby distending an outer wall of the body cavity or hollow organ, and a resistance meter for measuring electrical resistance across the balloon wall, whereby an indication of rupture of the balloon can be provided. Such a device can be usefully combined with any or all of the features described herein in connection with the first aspect. The resistance meter may be connected to a controller that provides an alert indicating a rupture of the balloon in reaction to a drop in resistance.

Viewed from a second aspect, the invention provides a method comprising use of the catheter device of the first aspect in the photodynamic treatment of a body cavity or hollow organ. The method may include the use of a device having any or all of the preferred features set out above.

The method generally includes insertion of the catheter device to an appropriate extent into the body cavity or hollow organ of interest, expanding the body cavity or hollow organ using the expansion and positioning balloon, and irradiating an internal surface of the body cavity or hollow organ with light from the light source.

In a preferred embodiment, the method includes administration of a photosensitiser or precursor of a photosensitiser to a patient in need of such photodynamic treatment. Such administration may be a systemic administration, i.e. parenteral administration, e.g. intramuscular or intravenous administration. Preferably the method includes local administration to the body cavity or hollow organ, e.g. instillation of a photosensitiser or precursor of a photosensitiser into the body cavity or hollow organ prior to insertion of the catheter device, or whilst the catheter device is inserted, optionally using a lumen of the catheter device to instil the photosensitiser or precursor of a photosensitiser.

Alternatively the photosensitiser or precursor of photosensitiser may be applied to the body cavity or hollow organ by contact of the expandable structure or other parts of the catheter device with the internal surface of the body cavity or hollow organ. Example procedures are set out in more detail below, along with details of suitable photosensitisers or precursors of photosensitisers.

The method preferably includes providing a photosensitiser or precursor of a photosensitiser as a composition in soluble form and administration as a dissolved composition, preferably by the catheter to the body cavity or hollow organ. In this case the catheter device may be arranged so that the second balloon is used to retain the distal end in place in the body cavity or hollow organ whilst fluid is instilled into the body cavity or hollow organ via the catheter device in order to administer the photosensitiser or precursor of a photosensitiser. The expansion and positioning balloon may be in its deflated state during this process.

The method may include supplying the composition in a sealed package, e.g. a sealed glass vial, along with a solvent to prepare a dissolved composition and the catheter device, which can advantageously be a single use device.

The dissolved composition may be allowed to remain in the body as appropriate to achieve the required photosensitising effect. If a composition comprising a photosensitiser was instilled into the body cavity or hollow organ via the catheter device, said body cavity or hollow organ may be expanded immediately after instillation using the expansion and positioning balloon, and PDT may be carried out irradiating an internal surface of the body cavity or hollow organ with light from the light source. If a composition comprising a precursor of a photosensitiser was administered parentally or instilled into the body cavity or hollow organ, said precursor first needs to be converted to an active photosensitiser, e.g. to protoporphyrins, before PDT can be carried out. Hence it is preferred to have a delay between the administration of such compounds and the start of the irradiation (incubation time). The incubation time is generally 5 min to up to 12 hours, such as 10 min to 2 hours or 30 min to 1 hour and thereafter PDT may be carried out irradiating an internal surface of the body cavity or hollow organ with light from the light source.

In a third aspect, the invention provides a method of photodynamic treatment of a body cavity or hollow organ, the method comprising: administering a photosensitiser or precursor of a photosensitiser to a patient in need of said treatment, inserting a device according to the first aspect into the body cavity or hollow organ of interest, expanding the body cavity or hollow organ using the expansion and positioning balloon, and irradiating an internal surface of the body cavity or hollow organ with light from the light source. The method may include use of a device having any or all of the preferred features set out above. The method may include using the second balloon to retain the device in place and seal the body cavity or hollow organ whilst fluid is instilled into the body cavity or hollow organ, for example to flush out the body cavity or hollow organ before or after treatment, and/or to instil a photosensitising composition or a precursor of a photosensitiser.

Methods relating to use of the catheter device in PDT provide a new medical use for the photosensitiser or precursor thereof, and thus another aspect of the invention provides a composition comprising 5-ALA, a derivative of 5-ALA or a pharmaceutically acceptable salt thereof for use in a method for photodynamic therapy, the method comprising: administration of the composition to a patient in need of such a photodynamic therapy, inserting a device according to the first aspect into a body cavity or hollow organ of interest, expanding the body cavity or hollow organ using the expansion and positioning balloon, and irradiating an internal surface of the body cavity or hollow organ with light from the light source.

Preferred embodiments of the invention will now be described by way of example only and with reference to the accompanying drawings, in which:

FIG. 4 and FIG. 5 show a perspective view and a side view of the distal end of a catheter device with a partial cutaway of some elements so that the construction and layout of the device can more clearly be seen.

Figure 1:
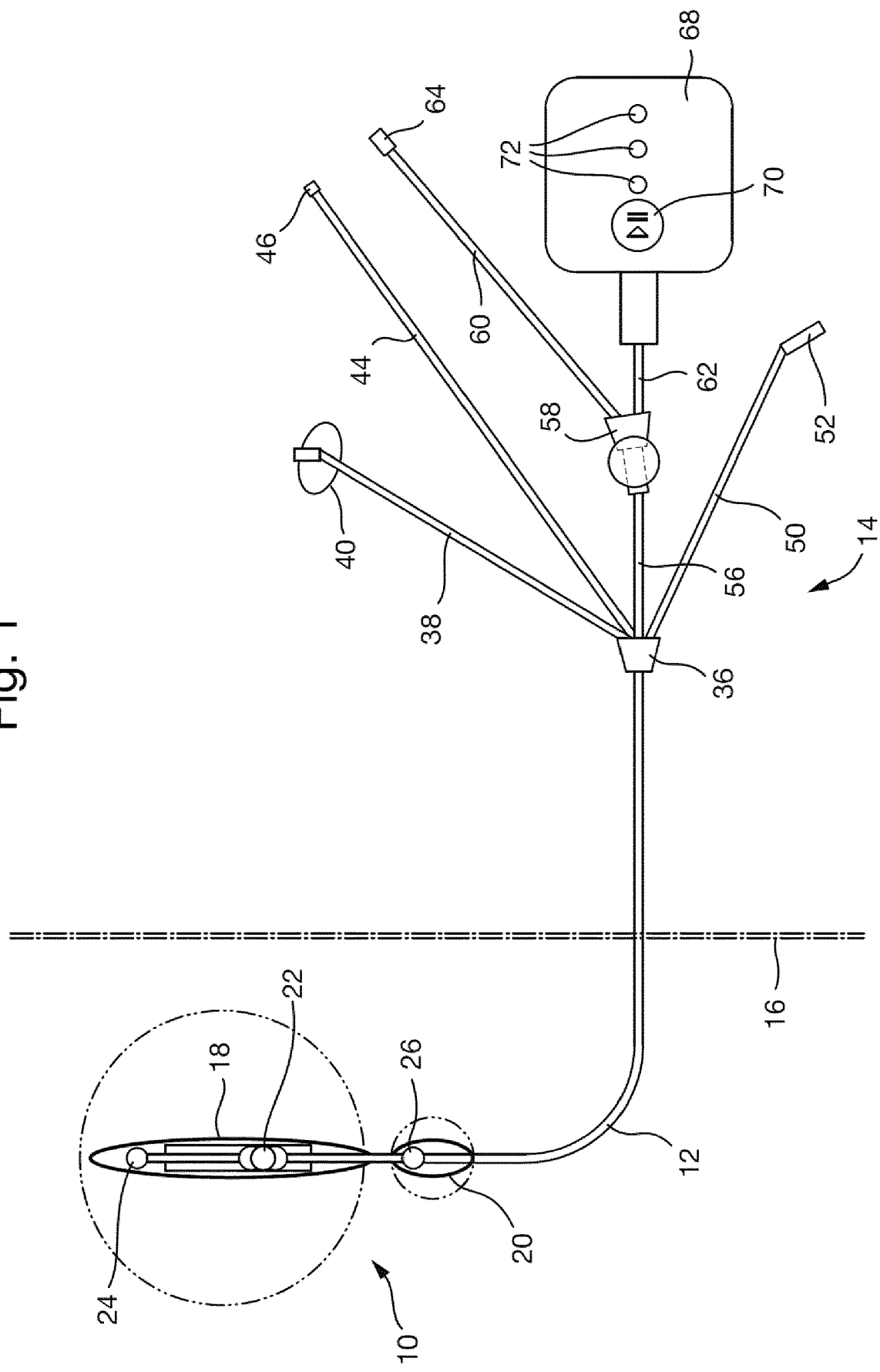
FIG. 1 shows a schematic overview of a catheter device including all parts to be provided to the user in preferably sterile packaging.
Figure 2:
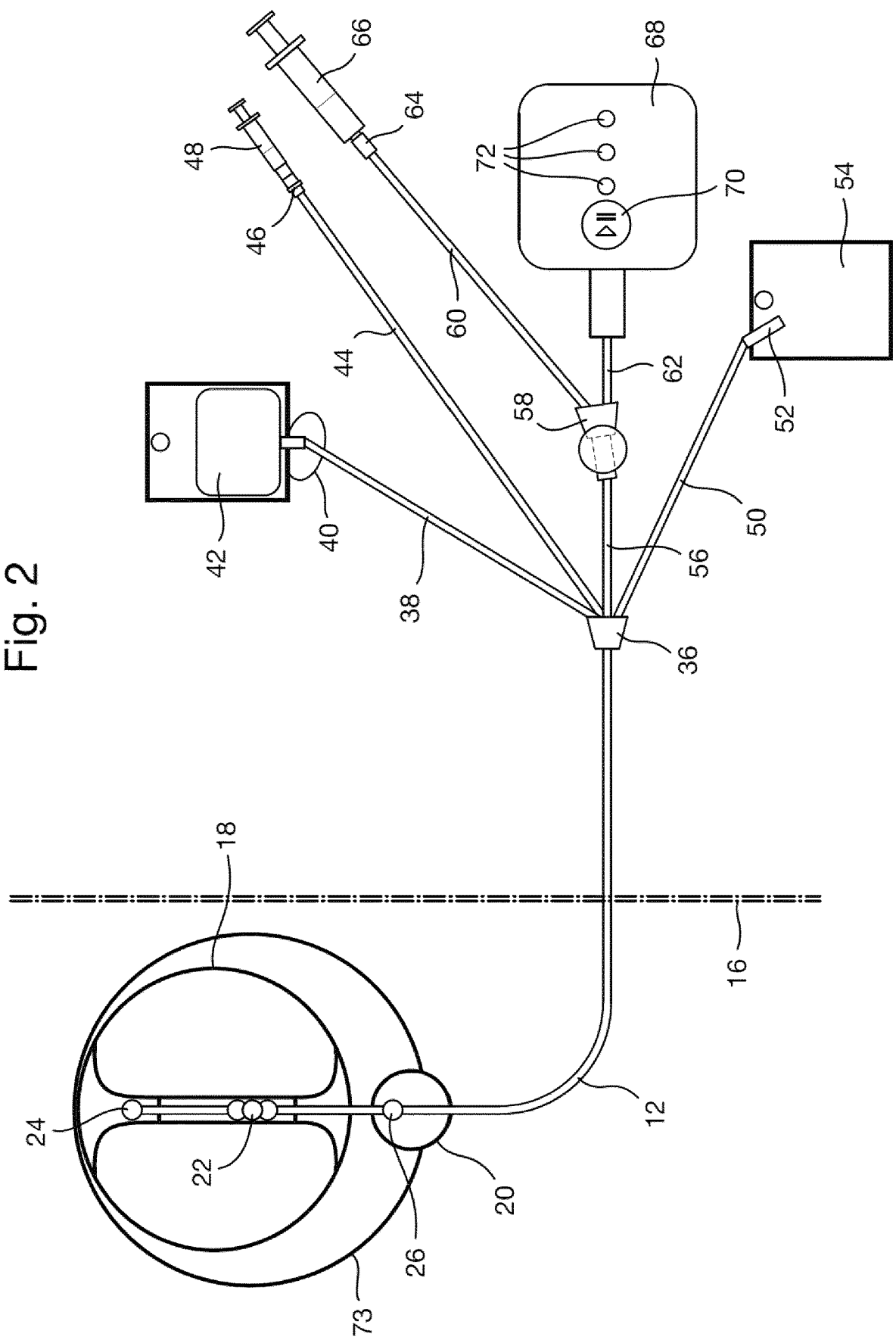
FIG. 2 shows a similar schematic with the catheter device in use, having its distal end inserted within and being provided with additional consumables.

With reference to FIG. 1 it will be seen that the catheter device consists of a distal end 10, a catheter body 12 extending from the distal end 10 to a proximal end 14, and various external elements at the proximal end 14. When in use, for example as shown in FIG. 2, the distal end 10 and a portion of the catheter body 12 are within a body cavity or hollow organ of a patient's body with the remainder of the catheter body 12 and the proximal end 14 with its external elements being at the outside of the patient's body. In FIG. 1 and FIG. 2 the divide between the parts that are internal to the patient's body and the parts that are external to the patient's body is shown by the vertical line 16. In this example the catheter device is adapted for use with the bladder and thus, by way of example, the geometry and size of the device relates to the bladder. It will however be appreciated that adaptations could easily be made to this device to arrive at a catheter device for treatment of other body cavities or hollow organs.

The catheter body 12 in this example is a multiple lumen catheter that is both flexible and is preferably disposable.

The diameter of the catheter may be any suitable size for the intended use and hence here the catheter is sized for insertion to the bladder. The diameter may be 8 mm or 9 mm, for example, but preferably it is lower and a preferred embodiment uses a 20 French catheter, i.e. diameter of 6.9 mm. The catheter and the wiring associated with providing power and control signals is flexible allowing for a bend radius as low as 25 mm.

The distal end 10, which is preferably disposable, includes an expansion and positioning balloon 18 and a Foley balloon 20. In this example the expansion and positioning balloon 18 is arranged to expand to a diameter of at least 58 mm with a volume of 99 mL. The Foley balloon 20 is arranged to expand to a diameter of 20 mm and have a volume of 3 mL.

The balloons 18, 20 may be made of latex formed on a mandrel. Alternative materials may be used, such as thermoplastic nylon materials. In some examples the material of the balloon skin includes a light attenuating medium such as a pigment or dye in order to allow for the degree of expansion of the balloon to vary the light dose as discussed above. The use of a light attenuating medium in the balloon skin can apply to the expansion and positioning balloon 18 and to the Foley balloon 20.

Figure 3:
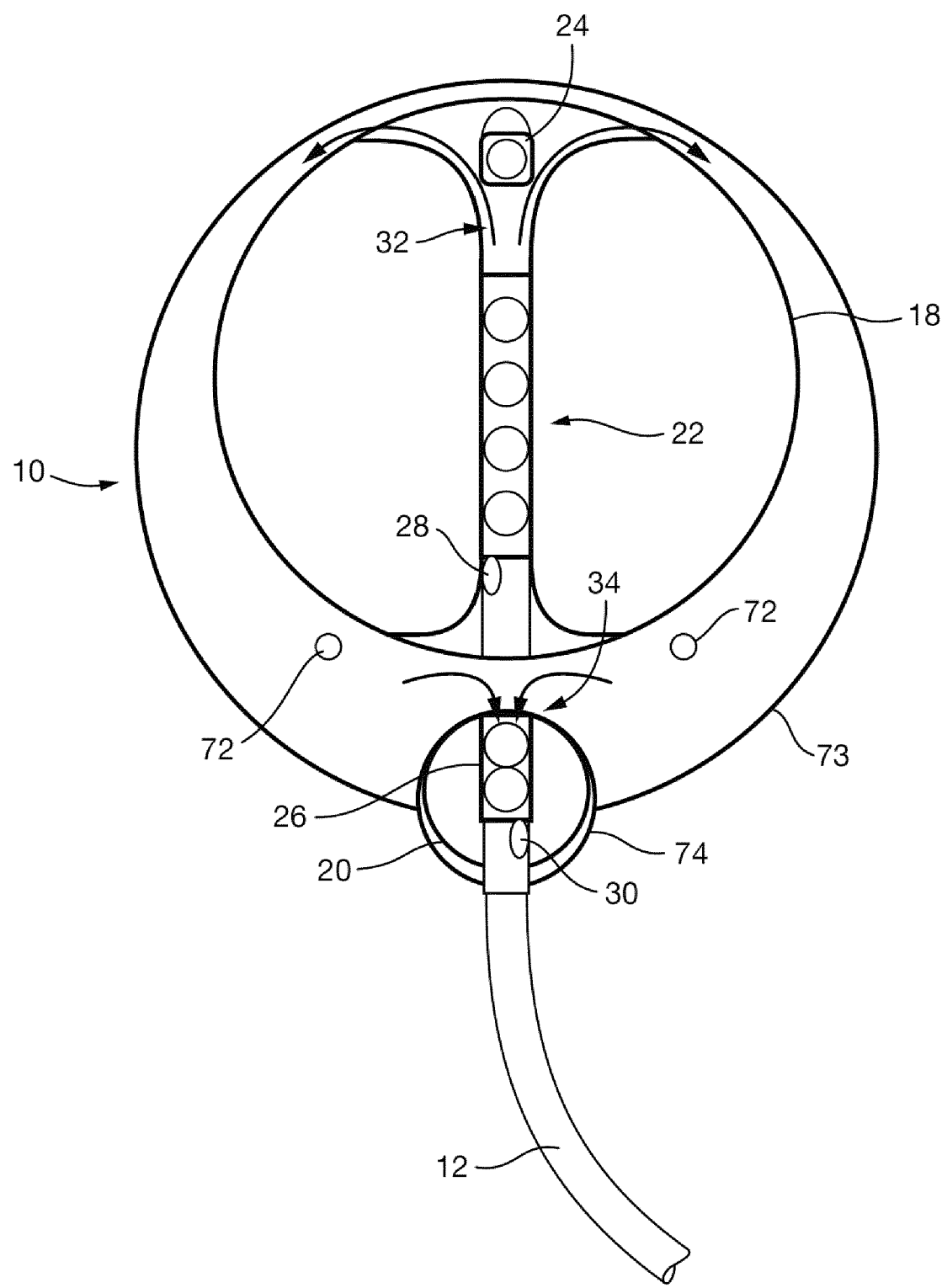
FIG. 3 shows a close-up view of the distal end of the catheter device in use, again in schematic view.

Preferred shapes for the expansion and positioning balloon 18 and for the Foley balloon 20 are discussed below with reference to FIGS. 4 and 5. FIG. 1 shows a very schematic indication of the balloons 18, 20 in their unexpanded shape, with a dashed line showing the expanded shape. FIGS. 2 and 3 show the balloons 18, 20 expanded with an indication of the position of the bladder wall 73 and, in FIG. 3, the trigone 74.

The distal end 10 also includes a light source for providing the necessary illumination for the required PDT. This light source comprises an array of light emitting elements, in this example LEDs, provided in three parts that are at three regions of the distal end. A central part 22 of the array of light emitting elements is at a second region of the distal end, this second region being within the expansion and positioning balloon 18. A distal part 24 of the array of light emitting elements is at a first region of the distal end 10, this first region being at a tip of the distal end and preferably being outside of the expansion and positioning balloon 18, as shown in more detail in FIG. 3 as well as in FIGS. 4 and 5, discussed below. A proximal part 26 of the array of light emitting elements is at a third region of the distal end 10, which in this example is within the Foley balloon 20, and which is at a location closer to the entry point of the catheter into the bladder than the second region.

Each of the three parts 22, 24, 26 of the array of light emitting elements includes multiple LEDs. For this example the LEDs are selected for the production of red light, e.g. red light at a wavelength of 635 nm. A possible arrangement for the LEDs is described below with reference to FIGS. 4 and 5. The arrangement of the LEDs for any required application can be determined by modelling of the light produced in order to achieve the required effect, which would typically be even illumination of a bladder target shape defined as nominally spherical of given diameter with a given target fluence rate and/or light dose for the required treatment. For this example the modelling might provide even illumination of a bladder target shape defined as nominally spherical of diameter approximately 70 mm and a target fluence rate in the range 15-25 mW/cm$^2$.

The distal end 10 additionally includes flow passages for flow of fluid into and out of the two balloons 18, 20 and for flow of fluid into and out of the bladder. In this example a single flow passage is provided for communication with each balloon, and hence fluid injected into the balloons and fluid extracted from the balloons passes in opposite directions through the same passage and in opposite directions through the same lumen within the catheter body 12. The catheter body 12 would hence include two lumens for supply of and for discharge of fluid from the two balloons 18, 20, a first lumen connecting to a passage 28 within the expansion and positioning balloon 18 and second lumen connecting to a passage 30 within the Foley balloon 20. The passages 28, 30 can be seen in FIG. 3 as well as in FIGS. 4 and 5. In addition to this, there is a separate inlet 32 and an outlet 34 (shown in FIGS. 3, 4 and 5) for fluid communication with the internal volume of the bladder 73 in order to allow for flushing of the bladder during PDT (for example to remove blood and the like that might impact on the effectiveness of the illumination), to drain urine and also potentially to allow for instillation (and draining) of the photosensitiser or precursor of the photosensitiser. The inlet 32 may also be used for injecting saline to act as lubricant fluid during expansion of the balloons. The inlet 32 in this example is close to the tip of the distal end 10, lying close to the distal part 24 of the array of light emitting elements. Flush fluids can circulate from the top of the expansion and positioning balloon 18 into the bladder 73, around the balloon 18 and then toward the outlet 34, which is located between the expansion and positioning balloon 18 and the Foley balloon 20 as shown most clearly in FIG. 3. The catheter body 12 would therefore require a further two lumens for separate supply of fluid to and discharge of fluid from the bladder. This embodiment hence requires four lumens in total for movement of fluids along the catheter body 12.

In relation to the parts of the catheter device 10 that lie outside of the patient's body when the device is in use, with reference to FIG. 1 and FIG. 2 it will be seen that the catheter body is provided with a splitter 36 at its proximal end, in this example a four-way splitter 36. After the splitter 36 fluid flow paths from the four lumens within the catheter body 12 are separated. A first conduit 38 for introducing flush fluids extends toward a flush fluid connector 40, which in use can be connected to a reservoir for supply of flush fluids, for example a drip type arrangement 42, shown in FIG. 2.

A second conduit 44 for injection of fluid into the Foley balloon 20 extends towards a Foley balloon fluid supply connector 46, which in use can be connected to a reservoir for supply of a fluid, for example saline, to the Foley balloon 20. The reservoir for supplying saline to the Foley balloon 20 may be a manually operated syringe 48, for example (shown in FIG. 2). The use of a manual syringe is preferred since this allows the catheter device to be operated in accordance with usual procedures for known catheters and without the need for special training or special equipment.

A third conduit 50 extends towards a fluid discharge connector 52 and is for discharge of (flush) fluids from the bladder. When in use the fluid discharge connector 52 may be attached to an appropriate collection reservoir such as a bag 54 as shown in FIG. 2.

The final, fourth, conduit 56 extends towards a further splitter, in this example a two way splitter 58, which acts to separate out a flow line 60 for supplying fluid to the expansion and positioning balloon 18 from a communications conduit 62 that carries wires for control signals and supply of power. In this example the fluid for the expansion and positioning balloon 18 travels along the same conduit 56 as the wires since the main electrical connections at the distal end are found in close proximity to the flow passage 28 that opens into the expansion and positioning balloon 18. The flow line 60 extends towards a connector 64 that, in use, is connected to a reservoir for supply of a fluid, such as saline, to the expansion and positioning balloon 18. As for the Foley balloon 20 this reservoir is advantageously a manually operated syringe 66. Naturally, the volume of the syringe 66 for the expansion and positioning balloon 18 is somewhat larger than the volume of the syringe 48 for the Foley balloon 20. Typically, the Foley balloon syringe 48 might have a volume of 5 mL and the expansion and positioning balloon syringe 66 might have a volume of 100 mL.

The communications conduit 62 connects to a controller 68, which in this example also includes a battery as a power source for the light source. The controller 68 includes a control button 70 as well as LED indicators 72 providing a means to display feedback to the user. Since the device is designed and intended for single use then the control button 70 may have only a small number of functions, in particular it may start the light illumination, i.e. PDT treatment and it may also be able to pause or stop the light illumination for example in the event of an adverse reaction by the patient. The LED indicators 72 may illuminate to provide an indication of on-going illumination, the amount of time elapsed in the treatment, or the amount of time remaining, and they may also be used to indicate faults or alerts and provide additional information. For example the LEDs may be used for indicating battery condition, showing if the device is in a pulsed mode of illumination, and indicating faults or alerts such as an excessive temperature, a potentially ruptured balloon, and so on.

In order to monitor temperature and pressure the distal end 10 may include one or more temperature or pressure sensor at an appropriate location. The temperature of the fluid inside or outside of the balloon(s) 18, 20, the temperature of the body of the distal end, or the temperature of a PCB holding the light emitting elements may be measured, with a calculation then being made to relate this to a temperature of the wall of the bladder, and an alert being provided if the measured temperature indicates a potentially excessive temperature at the wall of the body cavity or hollow organ, for example a temperature over 43° C. A pressure sensor may be used to measure the pressure within one or both balloons in order to provide an indication of potential leakage or rupture, which would result in an unexpected change in the pressure. An additional pressure sensor may measure pressure within the bladder fluid outside of the balloon(s) with a differential between the pressure inside a balloon and the pressure outside of the balloon being used to determine if there has been a breach of the balloon. An alert may be provided by the control circuit in the event that the pressure sensor(s) provide readings indicative of a breach of a balloon.

Wiring from the controller 68 passes along the communications conduit 62 and then along the fourth conduit 56 into the catheter body 12, where the wires are held either within one or more lumens or are embedded in the walls of the catheter body 12 and re-emerge at the distal end 10, where they are electrically connected to the light source and the temperature/pressure sensors.

The catheter device in FIG. 1 is advantageously provided for single-use and hence is disposable. This includes the controller 68, which may have features limiting it to a single-use, for example the circuit may prevent repeated activation after a treatment cycle has been completed.

As noted above, FIG. 3 shows a close-up of the distal end 10 of the catheter device with the balloons 18, 20, expanded and the distal end 10 in position within the bladder 73. The main features of the distal end 10 have already been described above. It will be recalled that a gap between the Foley balloon 20 and the expansion and positioning balloon 18 allows for fluid to flow easily into the outlet 34 for the (flush) fluids as shown by the arrows. This also avoids any obstruction of the bladder ureteral opening 72 by the balloons 18, 20. The Foley balloon 20 sits within the bladder trigone 74, which means that the proximal part 26 of the light source, which is located within the Foley balloon 20, can effectively provide illumination within and around the bladder trigone 74.

It will be seen that the central part 22 of the array of light emitting elements, which is in the expansion and positioning balloon 18, sits generally centrally within the bladder and is well-positioned to illuminate the majority of the bladder wall 73. The proximal part 26 of the array of light emitting elements addresses a shadow that would arise in the proximal direction along the distal end 10 from the central part 22. Likewise, the distal part 24 of the array of light emitting elements, which is located at the tip of the distal end 10 eliminates any shadow that would arise in the distal direction along the distal end 10 from the central part 22. Since the distal part 24 and the proximal part 26 are positioned closer to the bladder tissue than the central part 22, then the central part 22 uses higher intensity light whereas the proximal and distal parts use lower intensity light, the required difference in intensity can be achieved by the use of LEDs of different power/light intensity.

FIG. 3 also shows more detail of the shape of the balloons when expanded. The expansion and positioning balloon 18 forms a toroidal type shape with a generally spherical outer profile and hollows at the proximal and distal end similar to the hollows found in a horn torus or spindle torus. The first region, with the distal part 24 of the array of light emitting elements, sits in the hollow in the expansion positioning balloon 18 at the distal end of the balloon 18. This allows the balloon 18 to protect the bladder wall from contact with the distal part 24 of the array of light emitting elements. It should be noted that the Foley balloon 20 can also take a similar toroidal type shape, although it preferably is more spherical.

FIGS. 4 and 5 show the distal end 10, with the balloons in their unexpanded form, in a more accurate and less schematic example. The same basic features are present. Thus, the distal part 24 of the array of light emitting elements sits at the tip of the distal end 10 just beyond an inlet 32 for flush fluids. The expansion and positioning balloon 18 is joined to the body of the distal end 10 below the inlet 32 for flush fluids and at either side of a central part 22 of the light source. A flow passage 28 for injection of fluid into the expansion positioning balloon 18 is located within the expansion and positioning balloon 18. Below the expansion positioning balloon 18 (i.e. in the proximal direction) the outlet 34 for (flush) fluids being discharged from the bladder is positioned between the expansion and positioning balloon 18 and the Foley balloon 20. The Foley balloon is attached to the body of the distal end 10 on either side of a proximal part 26 of the array of light emitting elements and a flow passage 30 for injection of fluid into the Foley balloon 20 is within the Foley balloon 20. The catheter body 12 extends from the proximal part of the distal end toward the proximal part of the device and the external elements (not shown) which would be as described in relation to FIG. 1 and FIG. 2 above.

In the embodiment of FIG. 4 and FIG. 5 the distal part 24 of the array of light emitting elements includes LEDs in a dome like structure 80 for directing light in the distal direction along the longitudinal axis of the distal end 10 and also illuminates a region around the distal direction in a spherical segment. The central part 22 of the array of light emitting elements is made up of a flexible PCB wrapped to form a cylinder and having four rings each made of four LEDs 76, thereby directing light in all directions around and away from the longitudinal axis of the distal end 10. The proximal part 26 of the array of light emitting elements is made of LEDs 78 placed about the circumference of the body of the distal end 10 within the Foley balloon 20. As discussed above in connection with FIG. 3, the LEDs within the dome like structure 80 in the distal part of the array of light emitting elements and the LEDs 78 in the proximal part of the array of light emitting elements will be closer to the tissue of the bladder wall than the LEDs 76 in the central part 22. Therefore, the LEDs 76 will be of higher power/higher intensity than the LEDs in the proximal part 26 and the distal part 24.

Since the LEDs are in contact with liquids when the device is in use then they should be sealed against ingress of liquid, as should the associated electrical wiring/circuitry. This can be done via a layer of resin or plastic.

FIG. 4 and FIG. 5 also show more effectively a preferred form for the balloons 18, 20 in their unexpanded shape. The shape can be formed out of a suitable elastic material, such as latex, by means of a mandrel. For both balloons 18, 20 the general features of the shape are the same. The balloon is bonded to the main body of the distal end 10 at two outer tubular sections of lesser diameter. A central tubular section of greater diameter than the outer sections sits across the centre of the balloon, and in this case over the central part or proximal part of the light source. Two sections of varying diameter join the tubular sections. A balloon of this form when unexpanded will take the required toroidal type shape when it is filled with fluid and expanded.

When in use the catheter device is inserted into the body in conventional fashion for a catheter. Before inserting the catheter device, it may be coated with an analgesic, e.g. lidocaine. There is no general anaesthesia required, but the physician may decide to use a local anaesthetic. The user may be able to judge when the distal end 10 has reached the bladder (or other target body cavity or hollow organ) based on their experience and training, or alternatively in difficult cases all for harder to reach body cavities or organs some form of guidance may be used, such as ultrasound imaging.

When the distal end is in place the Foley balloon 20 is inflated by means of the Foley balloon syringe 46. This ensures that the distal end cannot leave the bladder or other target organ, and it also facilitates correct location of the remaining parts of the distal end inside of the bladder. After inflation of the Foley balloon 20 it may be required to flush the bladder or to instil a photosensitising drug or precursor thereof. Saline may be injected to act as a lubricant during the inflation of the expansion and positioning balloon 18. At an appropriate point the expansion and positioning balloon 18 is inflated by injecting fluid from the expansion and positioning balloon syringe 64. After the required incubation time has passed, if applicable, the patient with then be ready for treatment. Illumination via the three parts 22, 24, 26 of the array of light emitting elements can be started by means of the controller 68, typically by pressing the button 70. The controller 68 will ensure that the light source emits light for the required period of time, to provide a required light dose, whilst also continually checking for any fault or failure, including monitoring temperature and pressure as discussed above. When the required illumination period has elapsed then the controller will indicate that the treatment has been completed and the catheter device may be removed. To remove the device fluid is removed from the expansion and positioning balloon 18 and from the Foley balloon 20 using the respective syringes and the catheter device can be extracted from the body in a conventional fashion.

The preferred PDT procedure starts with the administration of the photosensitiser or precursor of photosensitiser. The mode of administration is dependent on which photosensitiser or precursor is used and has been described earlier. Typically, administration can be done systemically, i.e. parenterally (infusion, injection), enterally (oral or rectal administration) or topically to the body cavity or hollow organ of interest. Photofrin, for instance, is preferably intravenously administered while ALA and ALA-esters are preferably topically or enterally administered, e.g. instilled as a solution into the body cavity/hollow organ (e.g. to the bladder), applied topically to the inner surface of the body cavity/hollow organ (e.g. to the vagina), orally ingested (e.g. stomach, intestines) or rectally administered (intestines).

Photosensitisers or precursors of photosensitisers are formulated with compatible excipients that are known in the art as described for instance in WO 96/28412, WO 99/53962, WO 2009/074811, WO 2010/072419, WO 2010/142456, WO 2010/142457, WO 2011/161220, WO 2012/004399 and WO 2014/020164. For parenteral administration the photosensitiser or precursor of photosensitiser can be formulated as a solution, preferably aqueous solution. For enteral administration, the photosensitiser or precursor of photosensitiser can be formulated as a solid for oral administration, e.g. a pill, tablet, powder, granulate, capsule or as a solid for rectal administration, e.g. a suppository. Alternatively, the photosensitiser or precursor of photosensitiser can be formulated as a semi-solid for oral or rectal administration, e.g. a gel, emulsion, foam or ointment. Further, the photosensitiser or precursor of photosensitiser can be formulated as a liquid for oral administration, e.g. a solution, suspension, syrup or for rectal administration, e.g. an enema. For topical administration, the photosensitiser or precursor of photosensitiser can be formulated as a liquid, e.g. a solution such as an aqueous and/or alcoholic solution or suspension, as a semi-solid, e.g. a cream, emulsion, lotion, ointment, gel, foam and paste or as a solid, e.g. a transdermal patch. In a preferred embodiment, the photosensitiser or precursor of a photosensitiser is instilled into the body cavity or hollow organ in the form of a dissolved composition, e.g. dissolved in an aqueous solution such as a buffer.

Alternatively, the expansion and positioning balloon may be coated with the photosensitiser or precursor of photosensitiser, preferably in the form of a dry deposit or film, such as described in WO 2012/004399.

In general, any known photosensitisers or precursors thereof can be used in a method of PDT wherein the devices proposed herein are used.

Typical such photosensitisers include dyes like hypericin and PVP hypericin, psoralens, porphyrins such as hematoporphyrins, protoporphyrins, uroporphyrins, coproporphyrins, benzoporphyrins or deuteroporphyrins, in particular Photofrin® (profimer sodium), photosan III or verteporfin; chlorins, including bacteriochlorins and isochlorins such as chlorine e6, talaporfin or temoporfin and phthalocyanines such as aluminium- and silicon phthalocyanines.

Typical such precursors of photosensitisers include 5-aminolevulinic acid (5-ALA) and certain derivatives thereof, e.g. 5-ALA esters, preferably derivatives or pharmaceutically acceptable salts thereof disclosed in WO 96/28412, WO 02/10120, WO 2005/092838, WO 2009/077960 and WO 2014/020164, all of which are incorporated by reference.

The term "5-ALA" denotes 5-aminolevulinic acid, i.e. 5-amino-4-oxo-pentanoic acid.

The term "precursor of 5-ALA" denotes compounds which are converted metabolically to 5-ALA and thus are essentially equivalent thereto. Thus the term "precursor of 5-ALA" covers biological precursors for protoporphyrin in the metabolic pathway for haem biosynthesis.

The term "derivative of 5-ALA" denotes chemically modified 5-ALA, i.e. 5-ALA having undergone a chemical derivation such as substitution of a chemical group or addition of a further chemical group to modify or change any of its physico-chemical properties such as solubility or lipophilicity. Chemical derivation is preferably carried out at the carboxy group of 5-ALA, at the amino group of 5-ALA or at the keto group of 5-ALA, more preferably at the carboxy group of 5-ALA. Preferred derivatives are 5-ALA esters.

The term "pharmaceutically acceptable salt" denotes a salt fulfils the requirements related to for instance safety, bioavailability and tolerability (see for instance P. H. Stahl et al. (eds.) Handbook of Pharmaceutical Salts, Publisher Helvetica Chimica Acta, Zurich, 2002)

Preferred derivatives of 5-ALA are esters of 5-ALA. Such compounds are generally known and described in the literature see, for example, WO 96/28412, WO 02/10120, WO 03/041673, WO 2009/077960 and WO 2014/020164 the contents of which are incorporated herein by reference.

Esters resulting from a reaction of 5-ALA with unsubstituted or substituted alkanols, i.e. alkyl esters and substituted alkyl esters, and pharmaceutically acceptable salts thereof, are especially preferred derivatives of 5-ALA for use in the preferred embodiments.

5-ALA esters and pharmaceutically acceptable salts thereof for use in the preferred embodiments may be prepared by any conventional procedure available in the art, e.g. as described in WO 96/28412, WO 02/10120, WO 03/041673, WO 2009/077960 and WO 2014/020164 and in N. Fotinos et al., Photochemistry and Photobiology 2006, 82, 994-1015 and the cited literature references therein.

The 5-ALA esters may be in the form of a free amine, e.g. $—NH_2$, $—NHR^2$ or $—NR^2R^2$ or preferably in the form of a pharmaceutically acceptable salt. Such salts preferably are acid addition salts with pharmaceutically acceptable organic or inorganic acids. Suitable acids include, for example, hydrochloric, nitric, hydrobromic, phosphoric, sulphuric, sulfonic and sulfonic acid derivatives, the salts of ALA-esters and the latter acids are described in WO 2005/092838, the entire contents of which are incorporated herein by reference. A preferred acid is hydrochloride acid, HCl. Further preferred acids are sulfonic acid and sulfonic acid derivatives. Procedures for salt formation are conventional in the art and are for instance described in WO 2005/092838.

For bladder PDT, one preferred photosensitiser is PVP hypericin and preferred precursors of a photosensitiser are 5-ALA, 5-ALA esters or pharmaceutically acceptable salts thereof. Preferred 5-ALA esters are $C_1$-$C_6$-alkyl substituted 5-ALA esters, such as methyl, ethyl, propyl, butyl, pentyl and hexyl 5-ALA ester, most preferably hexyl 5-ALA ester, and the 5-ALA esters disclosed in WO 2014/020164. Further, more preferred is the use of a pharmaceutically acceptable salt of the hexyl ester of 5-ALA, e.g. hexyl 5-ALA ester hydrochloride.

The concentration of the photosensitisers or precursors of photosensitisers for use in PDT methods wherein the catheter devices of the invention are used depends upon the nature of the photosensitiser or precursor of photosensitiser, the nature of the composition, the mode of administration, the organ and condition to be treated, and the subject to which it is administered and may be varied or adjusted according to choice. For precursors of photosensitisers, such as 5-ALA and esters of 5-ALA, generally, concentration ranges of 0.01 to 50% by weight, such as 0.05 to 20% by weight, or 1 to 10% by weight, e.g. 1 to 5% by weight, are suitable. The hexyl 5-ALA ester may be instilled into the bladder as a 8 mM solution of the hydrochloride salt in an aqueous buffer (2 mg/ml; 0.2% by weight) or PVP hypericin may be instilled into the bladder in a total amount of 0.25 mg hypericin bound to 25 mg PVP, reconstituted in 50 ml physiological sodium chloride solution (A. Kubin et al., Photochem Photobiol 2008, 84(6), 1560-1563).

Since precursors of photosensitisers first have to be intracellularly converted to photosensitisers, e.g. ALA and ALA-esters to protoporphyrins, such as protoporphyrin IX (PpIX), it is preferred to have a delay between the administration of such compounds and the start of the irradiation (incubation time). The incubation time is generally 5 min to up to 12 hours, such as 10 min to 2 hours or 30 min to 1 hour.

In some cases the catheter device may be inserted into the body cavity/hollow organ and a lumen therein may be used to instil/administer the photosensitiser or precursor of a photosensitiser to the body cavity/hollow organ. During the incubation time, the catheter device may preferably be kept in place, i.e. inside the body cavity/hollow organ. Alternatively, it is withdrawn. After the incubation time, the body cavity/hollow organ is distended by means of the expandable structure and the now smooth internal surface of the body cavity/hollow organ is irradiated with light. In other cases a separate catheter or other delivery means is used to instil the photosensitiser or precursor to the body cavity or hollow organ.

Prior to PDT, it may be necessary and/or advantageously to empty the body cavity/hollow organ, e.g. to empty the intestines by help of a bowel cleansing procedure, the bladder by draining urine or the stomach by fasting.

During PDT, body fluids such as urine or gastric acid may be drained from the body cavity/hollow organ by means of the drainage lumen which is an integral part of the catheter device, e.g. the via the outlet 34 and the conduit 50 towards a fluid discharge connector 52 which may be attached to an appropriate collection reservoir such as a bag 54 (as shown in FIG. 2). Further, during PDT there may be the need to rinse the body cavity/hollow organ, e.g. from blood. This may be done by installing a flush fluid, e.g. saline by means of an instillation lumen which is an integral part of the catheter device, e.g. via an inlet 32 and a conduit 38 for introducing flush fluids which extends toward a flush fluid connector 40, which in use can be connected to a reservoir for supply of flush fluids, for example a drip type arrangement 42 (as shown in FIG. 2).

The abnormalities, disorders and diseases which may be treated with photodynamic treatment using the proposed catheter devices include any malignant, pre-malignant and benign abnormalities or disorders on the internal surface of a body cavity or hollow organ which are responsive to photodynamic treatment.

As used herein the term "treatment" or "therapy" encompasses curative as well as prophylactic treatment or therapy.

In general, cells which are metabolically active are responsive to photodynamic treatment with a photosensitiser or precursor of a photosensitiser. Examples of metabolically active cells are cells that undergo an abnormal growth pattern such as increased number of cells/increased cell proliferation (hyperplasia), wherein the cells of a hyperplastic growth remain subject to normal regulatory control mechanisms; abnormal maturation and differentiation of cells (dysplasia); and abnormal proliferation of cells (neoplasia), wherein genetically abnormal cells proliferate in a non-physiological manner which is unresponsive to normal stimuli. Other examples of metabolically active cells are infected or inflamed cells.

The proposed catheter devices may be used in photodynamic treatment of neoplasms and tumours (benign, premalignant and malignant) on internal surfaces of body cavities and hollow organs. Examples of such neoplasms and tumours on internal surfaces of body cavities and hollow organs are neoplasms in the vagina, bladder, the colon, the stomach and the gallbladder.

Further, the proposed catheter devices may be used in photodynamic treatment of abnormalities, disorders or diseases associated with viral, bacterial and fungal infections of internal surfaces of body cavities and hollow organs such as vaginal or cervical intraepithelial neoplasia (associated with the human papilloma virus), stomach cancer (associated with the bacterium *Helicobacter pylori*) and pseudomembranous colitis (associated with the bacterium *Clostridium difficile*).

In addition, the proposed catheter devices may be used in photodynamic treatment of abnormalities, disorders or diseases associated with inflamed cells. Inflammation is usually a protective attempt by the organism to remove the injurious stimuli and to initiate the healing process and thus often associated with an infection. Examples are inflammatory colitis (e.g. inflammatory bowel disease, ulcerative colitis and Crohn's disease)

The internal surfaces which may be treated by photodynamic treatment wherein the proposed catheter devices may be used are the internal surfaces of body cavities and hollow organs that comprise rugae, preferably the bladder, the gallbladder, the intestines, the stomach, and the vagina, most preferably the bladder.

In a preferred embodiment, the catheter device of the invention is for photodynamic treatment of bladder cancer, preferably superficial, non-muscle invasive bladder cancer such as papillary lesions and carcinoma in situ.

The invention claimed is:

1. A catheter device for use in the photodynamic treatment of the bladder, the catheter device comprising:
   a distal end portion having a longitudinal axis and being for insertion into the bladder, the distal end portion including:
   (a) a light source located on the distal end portion so as to be within the bladder when the catheter device is in use; wherein the light source comprises a plurality of light emitting elements arranged to:
      (i) project light forward in a distal direction along the direction of the longitudinal axis from a first region of the distal end,
      (ii) project light outwardly of the longitudinal axis from a second region of the distal end, the second region being at least partly within the expansion and positioning balloon; and
      (iii) project light around a point of entry of the catheter device into the bladder from a third region of the distal end, the third region being closer to the point of entry of the catheter device into the bladder than the second region;
   (b) an expansion and positioning balloon for correct positioning of the device within the bladder and for ensuring a suitable distance between a tissue of said bladder and the light emitting elements, wherein the expansion and positioning balloon is arranged to expand to a spheroidal or toroidal shape with an expanded diameter of between 60 mm and 100 mm within the bladder and thereby distending the bladder and resulting in a distended shape of the bladder, and wherein the expansion and positioning balloon is arranged to centre the device in relation to the distended shape of the bladder such that a required minimum light dose is applied for all parts of the interior of the bladder; and
   (c) the distal end portion further including a second balloon for retaining the distal end within the bladder, the second balloon being spaced apart from the expansion and positioning balloon and centred on a location closer to a proximal end of the catheter device than a centre of the expansion and positioning balloon.

2. The catheter device as claimed in claim 1, wherein the light source is powered by a battery or a low voltage power source that is, in use, outside of the body.

3. The catheter device as claimed in claim 1, wherein light emitting diodes (LEDs) are used as some or all of the light emitting elements.

4. The catheter device as claimed in claim 1, wherein the first region is outside of the expansion and positioning balloon the third region is outside the expansion and positioning balloon and the second region is at least partly inside, or fully inside the expansion and positioning balloon.

5. The catheter device as claimed in claim 1, wherein the plurality of light emitting elements includes at least one light emitting element at each of the first region, the second region and the third region, with the light emitting elements located at each region providing the light that is projected from that region.

6. The catheter device as claimed in claim 5, wherein the light emitting elements are arranged in an array having multiple parts including some or all of a first, distal part located at the first region for projecting light forward in the distal direction, a second, central part located at the second region for projecting light outwardly from the longitudinal axis of the distal end of the catheter device, and a third, proximal part located at the third region for projecting light around the point of entry of the catheter device into the bladder.

7. The catheter device as claimed in claim 6, wherein the first part of the array is at the tip of the distal end of the catheter device, and includes a light emitting element at the tip facing in the distal direction, the second part of the array includes a plurality of light emitting elements spaced around and along the longitudinal axis of the distal end, and the third part of the array includes a plurality of light emitting elements spaced around and along the longitudinal axis of the distal end.

8. The catheter device as claimed in claim 7, wherein the second part of the array comprises a flexible printed circuit board holding the light emitting elements, the flexible printed circuit board being wrapped in a cylindrical fashion in order to form a generally cylindrical shape holding the light emitting elements of the central part.

9. The catheter device as claimed claim 1, wherein the second balloon is for expansion at the point of entry of the catheter device into the bladder in order to prevent flow of fluid through a tubular body structure through which the catheter device is inserted and in order to secure the distal end of the catheter device in place within the bladder.

10. The catheter device as claimed claim 1, wherein the third region of the distal end is partially or fully within the second balloon, thereby ensuring that when the catheter device is in use the third region will be located at a known position relative to the point of entry of the catheter device into the bladder.

11. The catheter device as claimed in claim 1, wherein at least one of the expansion and positioning balloon or the second balloon has a balloon skin comprising a light attenuating medium, such that the attenuation of light passing through the balloon skin varies depending on the level of inflation of the balloon in order to permit regulation of a light dose based on the level of inflation of the balloon.

12. The catheter device as claimed in claim 1, wherein the expansion and positioning balloon is a sheath along and around a part of the distal end when it is in its unexpanded form.

13. The catheter device as claimed in claim 1, wherein the distal end of the catheter device is provided with at least one fluid inlet/outlet within one or more of the balloons, such that the one or more balloons can be expanded by injecting a fluid into the balloon via the catheter device.

14. The catheter device as claimed in claim 1, wherein the distal end comprises a fluid inlet and a fluid outlet for communication with the inside of the bladder.

15. The catheter device as claimed in claim 1, comprising an elongate catheter body extending from the distal end to a proximal end of the catheter device, wherein the elongate catheter body includes lumens for transport of fluid to and from the various outlets.

16. The catheter device as claimed in claim 15, wherein the elongate catheter body includes one or more lumen for passage of electrical wires.

17. The catheter device as claimed in claim 15, wherein the catheter body includes lumens for passage of fluid and wires embedded in walls of the catheter body.

18. The catheter device as claimed in claim 1, wherein the proximal end of the catheter body is coupled to one or more external elements including a power source, one or more fluid reservoirs for inflation of the balloons(s) and/or for instilling fluid into the bladder, a receptacle for receiving fluids flushed from the bladder, and/or a controller.

19. The catheter device as claimed in claim 1, wherein a pressure activated device is provided at the proximal end of the catheter body in order to provide an indication and/or a release of pressure in the event that the pressure within the expansion and positioning balloon and/or within the second balloon exceeds a threshold level.

20. The catheter device as claimed in claim 1, including as an external element a controller the controller including a control circuit for controlling the light source and for providing indications relating to operation of the device, wherein the catheter device includes one or more sensors for measuring a parameter relating to the performance of the device.

21. The catheter device as claimed in claim 1, wherein the plurality of light emitting elements are able to produce irradiation with wavelengths of light in the range of 300-800 nm.

22. A kit comprising the catheter device of claim 1 and a photosensitiser or precursor thereof.

23. A method of photodynamic therapy of a bladder, the method comprising: administration of a composition comprising 5-ALA, a derivative of 5-ALA or a pharmaceutically acceptable salt thereof to a patient in need of such a photodynamic therapy, inserting the device according to claim 1 into the bladder, expanding the bladder using the expansion and positioning balloon, and irradiating an internal surface of the bladder with light from the light source.

* * * * *